US009729833B1

(12) United States Patent
Kusens (10) Patent No.: US 9,729,833 B1
(45) Date of Patent: Aug. 8, 2017

(54) METHOD AND SYSTEM FOR DETERMINING WHETHER AN INDIVIDUAL TAKES APPROPRIATE MEASURES TO PREVENT THE SPREAD OF HEALTHCARE-ASSOCIATED INFECTIONS ALONG WITH CENTRALIZED MONITORING (71) Applicant: CERNER INNOVATION, INC., Kansas City, KS (US)

(72) Inventor: Neil Kusens, Sherman Oaks, CA (US)

(73) Assignee: CERNER INNOVATION, INC., Kansas City, KS (US)

( * ) Notice: Subject to any disclaimer, the term of this patent is extended or adjusted under 35 U.S.C. 154(b) by 211 days.

(21) Appl. No.: 14/613,866

(22) Filed: Feb. 4, 2015

Related U.S. Application Data (63) Continuation-in-part of application No. 14/599,498, filed on Jan. 17, 2015.
(Continued)

(51) Int. Cl.
*H04N 7/18* (2006.01)
*H04N 13/02* (2006.01)
(Continued)

(52) U.S. Cl.
CPC .......... *H04N 7/18* (2013.01); *G06F 17/3028* (2013.01); *G06K 9/00342* (2013.01);
(Continued)

(58) Field of Classification Search
CPC .. H04N 7/18; H04N 13/0203; G06K 9/00342; G06T 7/0051; G06T 7/0012; G06T 7/2086; G06F 17/3028
See application file for complete search history.

(56) References Cited

U.S. PATENT DOCUMENTS

| 4,857,716 A | 8/1989 | Gombrich et al. |
| 5,031,228 A | 7/1991 | Lu |

(Continued)

FOREIGN PATENT DOCUMENTS

| DE | 19844918 A1 | 4/2000 |

OTHER PUBLICATIONS

Pending U.S. Application by same inventor Neil Kusens, U.S. Appl. No. 14/084,588, filed Nov. 19, 2013, entitled "Method for Determining Whether an Individual Leaves a Prescribed Virtual Perimeter".
(Continued)

*Primary Examiner* — Sath V Perungavoor
*Assistant Examiner* — Howard D Brown, Jr.
(74) *Attorney, Agent, or Firm* — Shook, Hardy & Bacon, LLP (57) ABSTRACT

A system and method that caregivers, central monitoring companies and other persons to monitor whether individuals entering patients' rooms take appropriate steps to mitigate the spread of healthcare associated infections to the patients receiving healthcare services. In one non-limiting the system and method determine whether an individual who has entered the room of a patient has wash his or her hands prior to approaching the patient. A live video feed from the monitored rooms can be displayed on a centralized monitoring primary display which can be located remote to the monitored rooms. When it is determined that an individual in a specific room from the monitored rooms is approaching a patient and has not washed his or her hands an alert, notification and/or a live video feed for the specific room can be displayed on a centralized monitoring alert display which can also be preferably located remote to the monitored rooms.

20 Claims, 9 Drawing Sheets

Related U.S. Application Data (60) Provisional application No. 61/935,450, filed on Feb. 4, 2014, provisional application No. 61/928,485, filed on Jan. 17, 2014.

(51) Int. Cl.
*G06K 9/00* (2006.01)
*G06T 7/20* (2017.01)
*G06T 7/00* (2017.01)
*G06F 17/30* (2006.01)
*G08B 23/00* (2006.01)

(52) U.S. Cl.
CPC .......... *G06T 7/0012* (2013.01); *G06T 7/0051* (2013.01); *G06T 7/2086* (2013.01); *H04N 13/0203* (2013.01)

(56) References Cited

U.S. PATENT DOCUMENTS

| | | | |
|---|---|---|---|
| 5,448,221 A | 9/1995 | Weller | |
| 5,482,050 A | 1/1996 | Smokoff et al. | |
| 5,798,798 A | 8/1998 | Rector et al. | |
| 5,915,379 A | 6/1999 | Wallace et al. | |
| 5,942,986 A | 8/1999 | Shabot et al. | |
| 6,050,940 A | 4/2000 | Braun et al. | |
| 6,095,984 A | 8/2000 | Amano et al. | |
| 6,160,478 A | 12/2000 | Jacobsen et al. | |
| 6,174,283 B1 | 1/2001 | Nevo et al. | |
| 6,188,407 B1 | 2/2001 | Smith et al. | |
| 6,269,812 B1 | 8/2001 | Wallace et al. | |
| 6,287,452 B1 | 9/2001 | Allen et al. | |
| 6,322,502 B1 | 11/2001 | Schoenberg et al. | |
| 6,369,838 B1 | 4/2002 | Wallace et al. | |
| 6,429,869 B1 | 8/2002 | Kamakura et al. | |
| 6,614,349 B1 | 9/2003 | Proctor et al. | |
| 6,727,818 B1* | 4/2004 | Wildman | G06F 19/3418 340/10.1 |
| 6,804,656 B1 | 10/2004 | Rosenfeld et al. | |
| 7,323,991 B1 | 1/2008 | Eckert et al. | |
| 7,612,679 B1 | 11/2009 | Fackler et al. | |
| 7,724,147 B2 | 5/2010 | Brown | |
| 7,756,723 B2 | 7/2010 | Rosow et al. | |
| 7,908,153 B2* | 3/2011 | Scherpbier | G06Q 10/06 600/300 |
| 7,945,457 B2 | 5/2011 | Zaleski | |
| 8,237,558 B2 | 8/2012 | Seyed Momen et al. | |
| 8,273,018 B1 | 9/2012 | Fackler et al. | |
| 8,432,263 B2 | 4/2013 | Kunz | |
| 8,529,448 B2 | 9/2013 | McNair | |
| 8,565,500 B2 | 10/2013 | Neff | |
| 8,620,682 B2 | 12/2013 | Bechtel et al. | |
| 8,769,153 B2 | 7/2014 | Dziubinski | |
| 8,902,068 B2 | 12/2014 | Bechtel et al. | |
| 8,917,186 B1 | 12/2014 | Grant | |
| 9,072,929 B1 | 7/2015 | Rush et al. | |
| 9,129,506 B1 | 9/2015 | Kusens | |
| 9,159,215 B1 | 10/2015 | Kusens | |
| 9,538,158 B1 | 1/2017 | Rush et al. | |
| 2002/0015034 A1 | 2/2002 | Malmborg | |
| 2002/0077863 A1 | 6/2002 | Rutledge et al. | |
| 2002/0183976 A1 | 12/2002 | Pearce | |
| 2003/0037786 A1 | 2/2003 | Biondi et al. | |
| 2003/0070177 A1 | 4/2003 | Kondo et al. | |
| 2003/0092974 A1 | 5/2003 | Santoso et al. | |
| 2003/0095147 A1 | 5/2003 | Daw | |
| 2003/0140928 A1 | 7/2003 | Bui et al. | |
| 2003/0227386 A1 | 12/2003 | Pulkkinen et al. | |
| 2004/0019900 A1 | 1/2004 | Knightbridge et al. | |
| 2004/0052418 A1 | 3/2004 | DeLean | |
| 2004/0054760 A1 | 3/2004 | Ewing et al. | |
| 2004/0097227 A1 | 5/2004 | Siegel | |
| 2004/0116804 A1 | 6/2004 | Mostafavi | |
| 2004/0193449 A1 | 9/2004 | Wildman et al. | |
| 2005/0038326 A1 | 2/2005 | Mathur | |
| 2005/0249139 A1 | 11/2005 | Nesbit | |
| 2006/0004606 A1 | 1/2006 | Wendl | |
| 2006/0089541 A1 | 4/2006 | Braun et al. | |
| 2006/0092043 A1 | 5/2006 | Lagassey | |
| 2006/0107295 A1 | 5/2006 | Margis et al. | |
| 2006/0145874 A1 | 7/2006 | Fredriksson et al. | |
| 2006/0261974 A1 | 11/2006 | Albert et al. | |
| 2007/0085690 A1 | 4/2007 | Tran | |
| 2007/0279219 A1 | 12/2007 | Warriner | |
| 2008/0002860 A1 | 1/2008 | Super et al. | |
| 2008/0087719 A1 | 4/2008 | Sahud | |
| 2008/0249376 A1 | 10/2008 | Zaleski | |
| 2009/0091458 A1 | 4/2009 | Deutsch | |
| 2009/0099480 A1 | 4/2009 | Salgo et al. | |
| 2009/0224924 A1* | 9/2009 | Thorp | G08B 21/245 340/573.1 |
| 2009/0278934 A1 | 11/2009 | Ecker et al. | |
| 2009/0322513 A1 | 12/2009 | Hwang et al. | |
| 2010/0117836 A1* | 5/2010 | Seyed Momen | G01S 1/70 340/573.1 |
| 2010/0176952 A1 | 7/2010 | Bajcsy et al. | |
| 2010/0188228 A1* | 7/2010 | Hyland | G08B 21/22 340/573.1 |
| 2010/0205771 A1 | 8/2010 | Pietryga et al. | |
| 2010/0285771 A1 | 11/2010 | Peabody | |
| 2011/0018709 A1 | 1/2011 | Kornbluh | |
| 2011/0025493 A1 | 2/2011 | Papadopoulos et al. | |
| 2011/0025499 A1 | 2/2011 | Hoy et al. | |
| 2011/0087079 A1 | 4/2011 | Aarts | |
| 2011/0102133 A1 | 5/2011 | Shaffer | |
| 2011/0227740 A1 | 9/2011 | Wohltjen | |
| 2012/0026308 A1 | 2/2012 | Johnson et al. | |
| 2012/0092162 A1 | 4/2012 | Rosenberg | |
| 2012/0098918 A1 | 4/2012 | Murphy | |
| 2012/0212582 A1* | 8/2012 | Deutsch | G08B 21/245 348/46 |
| 2013/0120120 A1 | 5/2013 | Long et al. | |
| 2013/0122807 A1* | 5/2013 | Tenarvitz | H04B 5/0031 455/41.1 |
| 2013/0309128 A1* | 11/2013 | Voegeli | A61L 2/0088 422/3 |
| 2013/0332184 A1* | 12/2013 | Burnham | G06Q 10/0635 705/2 |
| 2014/0039351 A1 | 2/2014 | Mix et al. | |
| 2014/0070950 A1 | 3/2014 | Snodgrass | |
| 2014/0191861 A1 | 7/2014 | Scherrer | |
| 2014/0267625 A1 | 9/2014 | Clark et al. | |
| 2014/0327545 A1* | 11/2014 | Bolling | G08B 21/245 340/573.1 |
| 2014/0333744 A1* | 11/2014 | Baym | G08B 21/245 348/77 |
| 2014/0354436 A1 | 12/2014 | Nix et al. | |
| 2014/0365242 A1 | 12/2014 | Neff | |
| 2015/0206415 A1* | 7/2015 | Wegelin | G08B 21/245 340/573.4 |
| 2015/0278456 A1 | 10/2015 | Bermudez Rodriguez et al. | |
| 2016/0022218 A1 | 1/2016 | Hayes et al. | |
| 2016/0267327 A1 | 9/2016 | Franz et al. | |

OTHER PUBLICATIONS

Pending U.S. Application by same inventor Neil Kusens, U.S. Appl. No. 14/575,850, filed Dec. 18, 2014, entitled "Method and Process for Determining Whether an Individual Suffers a Fall Requiring Assistance".

Pending U.S. Application by same inventor Neil Kusens, U.S. Appl. No. 14/599,498, filed Jan. 17, 2015, entitled "Method and System for Determining Whether an Individual Takes Appropriate Measures to Prevent the Spread of Healthcare Associated Infections".

Pending U.S. Application by same inventor Neil Kusens, U.S. Appl. No. 14/611,363, filed Feb. 2, 2015, entitled "Method and System for Determining Whether an Individual Takes Appropriate Measures to Prevent the Spread of Healthcare Associated Infections".

Pending U.S. Application by same inventor Neil Kusens, U.S. Appl. No. 14/623,349, filed Feb. 16, 2015, entitled "Method for Determining Whether an Individual Enters a Prescribed Virtual Zone Using 3D Blob Detection".

(56) References Cited

OTHER PUBLICATIONS

Pending U.S. Application by same inventor Neil Kusens, U.S. Appl. No. 14/724,969, filed May 29, 2015, entitled "Method and Process for Determining Whether an Individual Suffers a Fall Requiring Assistance".
Pending U.S. Application by same inventor Neil Kusens, U.S. Appl. No. 13/543,816, filed Jul. 7, 2012, entitled "Method and Process for Determining Whether an Individual Suffers a Fall Requiring Assistance".
Pending U.S. Application by same inventor Neil Kusens, U.S. Appl. No. 14/727,434, filed Jun. 1, 2015, entitled Method for Determining Whether Enters a Prescribed Virtual Zone Using Skeletal Tracking and 3D Blob Detection.
Pending U.S. Application by same inventor Neil Kusens, U.S. Appl. No. 14/728,762, filed Jun. 2, 2015, entitled "Method for Determining Whether an Individual Leaves a Prescribed Virtual Perimeter".
Pending U.S. Application by same inventor Neil Kusens, U.S. Appl. No. 14/743,264, filed Jun. 18, 2015, entitled "System for Determining Whether an Individual Enters a Prescribed Virtual Zone Using 3D Blob Detection".
Pending U.S. Application by same inventor Neil Kusens, U.S. Appl. No. 14/743,499, filed Jun. 18, 2015, entitled "System for Determining Whether an Individual Suffers a Fall Requiring Assistance".
Pending U.S. Application by same inventor Neil Kusens, U.S. Appl. No. 14/743,447, filed Jun. 18, 2015, entitled "System for Determining Whether an Individual Suffers a Fall Requiring Assistance".
Pending U.S. Application by same inventor Neal Kusens. U.S. Appl. No. 14/611,363, filed Feb. 2, 2015, entitled "Method and System for Determining Whether an Individual Takes Appropriate Measures to Prevent the Spread of Healthcare Associated Infections".
Non-Final Office Action dated May 23, 2016 in U.S. Appl. No. 14/743,499, 5 pages.
Notice of Allowance dated May 31, 2016 in U.S. Appl. No. 14/743,447, 8 pages.
Notice of Allowance dated Jun. 22, 2016 in U.S. Appl. No. 14/743,447, 4 pages.
Notice of Allowance dated Jun. 27, 2016 in U.S. Appl. No. 14/728,762, 14 pages.
Notice of Allowance dated Jun. 5, 2015 in U.S. Appl. No. 13/543,816, 5 pages.
Non-Final Office Action dated Feb. 11, 2016 in U.S. Appl. No. 14/724,969, 14 pages.
Notice of Allowance dated Jul. 18, 2016 in U.S. Appl. No. 14/743,264, 16 pages.
Final Office Action dated Jul. 28, 2016 in U.S. Appl. No. 14/723,969, 26 pages.
Tom Mooney, "Rhode Island ER first to test Google Glass on medical conditions", http://www.ems1.com/ems-products/cameras-video/articles/1860487-Rhode-Island-ER-first . . . printed on Mar. 11, 2014.
Notice of Allowance dated Aug. 26, 2016 in U.S. Appl. No. 14/743,447, 5 pages.
Notice of Allowance dated Sep. 19, 2016 in U.S. Appl. No. 14/743,499, 5 pages.
Notice of Allowance dated Oct. 14, 2016 in U.S. Appl. No. 14/743,264, 14 pages.
Notice of Allowance dated Nov. 9, 2016 in U.S. Appl. No. 14/743,264, 14 pages.
Notice of Allowance dated Nov. 14, 2016 in U.S. Appl. No. 14/743,447, 5 pages.
Non-Final Office Action dated Oct. 7, 2015 in U.S. Appl. No. 14/339,397, 16 pages.
Non-Final Office Action dated Mar. 11, 2016 in U.S. Appl. No. 14/575,850, 10 pages.
Notice of Allowance dated Dec. 23, 2016 in U.S. Appl. No. 14/724,969, 5 pages.
Non-Final Office Action dated Jan. 11, 2017 in U.S. Appl. No. 14/611,363, 19 pages.
Non-Final Office Action dated Feb. 23, 2017 in U.S. Appl. No. 14/757,877, 24 pages.
First Action Interview Preinterview Communication dated Feb. 24, 2017 in U.S. Appl. No. 15/395,716, 5 pages.

* cited by examiner

METHOD AND SYSTEM FOR DETERMINING WHETHER AN INDIVIDUAL TAKES APPROPRIATE MEASURES TO PREVENT THE SPREAD OF HEALTHCARE-ASSOCIATED INFECTIONS ALONG WITH CENTRALIZED MONITORING

This application claims priority to and the benefit of U.S. Application Ser. No. 61/935,450, filed Feb. 4, 2014, and is a continuation-in-part of U.S. application Ser. No. 14/599,498, filed Jan. 17, 2015, which application claims priority to and the benefit of U.S. Provisional Application Ser. No. 61/928,485, filed Jan. 17, 2014. All of the above-identified applications are incorporated by reference in their entireties.

1. BACKGROUND

Healthcare-associated infections (HAIs) are infections that are acquired by patients during the course of receiving treatment for other health conditions. According to recent studies, one in every twenty hospitalized patients will acquire an infection during the course of receiving healthcare treatment for a different condition. In terms of the economic impact, studies estimate the overall annual direct medical costs of HAIs range between $28.4 and $45 billion. The medical facility must typically bear the cost of the HAI, which puts a strain on the finances of the healthcare provider.

2. SUMMARY AND DEFINITIONS

The disclosure describes a system and method that is directed to the above problems and provides for a system and method that allows caregivers, central monitoring companies and other persons to monitor whether individuals entering patients' rooms take appropriate steps to mitigate the spread of HAIs to the patients receiving healthcare services. In one non-limiting example, the system and method determine whether an individual who has entered the room of a patient has washed his or her hands prior to approaching the patient.

Non-limiting definitions that will be used in describing certain embodiments of the present invention include:

| | |
|---|---|
| 3D Motion and Sound Sensor | An electronic device that contains one or more cameras capable of identifying individual objects, people and motion regardless of lighting conditions, as well as one or more microphones to detect audio. The cameras can utilize technologies including but not limited to color RGB, CMOS sensors, infrared projectors and RF-modulated light, They may also contain microprocessors and image sensors to detect and process information both sent out and received by the various cameras.<br>The electronic device can calculate if there has been a change in location of a person or object of interest over a period of time. As a non-limiting example, a person's right knee can be at time T1 located at coordinates (x1 , y1, z1) in a picture frame taken by the camera. At time T2 the right knee is capture by the picture frame taken by the camera at coordinates (x2, y2, z2). Based on this information, motion, speed and direction can be derived utilizing the elapsed time and comparing the two 3D coordinates over the elapsed time. As opposed to conventional motion sensors, which use captured motion to control a camera, the 3D Motion and Sound Sensor used with the method and system, uses the camera in order to compute the motion.<br>The camera/sensors are preferably continuously on at all times while the monitoring is occurring, regardless of whether a person or object of interest is moving or not moving. The camera preferably views the entire room or a large portion of the room simply by its placement in a manner sufficient for the room to be visible to the camera.. Thus, the camera does not require any triggering event to cause the camera to begin recording video and/or 3D depth data or transmitting video and/or 3D depth data to the other components of the system for analysis. As the video camera is recording or otherwise transmitting video and/or 3D depth data to the other system components at all times during monitoring, the electronic device is able to immediately track, capture and/or record the individual's movements at all times within the patient's worn and will be able to provide information as to whether and when the individual enters the room, whether and when the individual washed his or her hands, whether and when the individual approaches the patients, whether and when the individual leaves the room, etc.<br>Preferably the 3D Motion and Sound Sensor records, captures and/or streams video and/or 3D depth data. As video is technically made up of individual picture frames (i.e, 30 frames per second of video), the above reference to picture frames is referring to frames of video.<br>The 3D Motion and Sound Sensor can be located within the room of the patient being monitored and potentially just outside of the patient's room. It is connected to the computerized communication and computerized monitoring systems via a data connection (TCP/IP or comparable technology). |
| Computerized Monitoring System | A computer system programmed to monitor activity of the 3D Motion and Sound sensor(s) The computerized monitoring system will preferably be located within the patient's room and can be connected to the centralized monitoring station at the facility but can also be located at any physical location so long as a data connection (TCP/IP or comparable technology) exists between the computerized monitoring system, the computerized communication system, and 3D motion and sound sensor. The computerized monitoring system |

| | |
|---|---|
| | preferably makes the determination of a whether and when the individual approaches the patient and whether and when the individual washed his or her hands prior to approaching the patient based on the data (video and/or 3D depth data) received by the video camera sensors, |
| Computerized Communication System | A computer system programmed to facilitate communication between the patient and/or individual and computerized monitoring system in the event it is determined that the individual did not wash his or her hands prior to approaching the patient or otherwise did not take appropriate measures to prevent or reduce the spread of healthcare-associated infections. This system may include but is not limited to amplified speakers, microphones, lights, monitors, computer terminals, mobile phones and or other technologies to allow for the electronic communication to take place. The system can also be designed to notify the individual that they need to wash their hands also through a text message or other electronic message sent to the individual's smart phone, pager, etc. The computerized communication system will preferably be located within the patient's room being monitored but certain components of the system are mobile by their nature (i.e. mobile phones, pagers, computers) and can also be located at any location so long as a data connection (TCP/IP or comparable technology) exists between the computerized monitoring system, the computerized communication system, and 3D motion and sound sensor. |
| Healthcare-associated infection (HAI) | Infections acquired by individuals while receiving, healthcare services in an institutional setting or other location where the healthcare services are being provided. |
| Centralized Monitoring Station | A computer system programmed to receive video, audio, 3D depth data and/or data streams from one or more computerized monitoring systems, computerized communication systems and/or 3D motion and sound sensors. The centralized monitoring station can process the information received from one or more computerized monitoring systems, computerized communication systems and/or 3D motion and sound sensors and display the information in an organized manner (in conjunction with a centralized monitoring primary display described below) to an individual or group of individuals assigned to monitor the patients. The computerized communication system can preferably be located within the facility where patients are being monitored but can also be located at any location so long as a data connection (TCP/IP or comparable technology) exists between the computerized monitoring systems, computerized communication systems, centralized monitoring station and 3D motion and sound sensors. |
| Centralized Monitoring Primary Display | A computer display connected to the centralized monitoring station, showing video and preferably also audio of all patient rooms connected to the centralized monitoring station. |
| Centralized Monitoring Alert Display | A computer display connected to the centralized monitoring station, showing video and preferably also audio of any patient room where it was determined that an individual is approaching or has approached a patient or has entered into a safety zone and such individual has not washed their hands or otherwise taken appropriate measures to prevent or reduce the spread of healthcare-associated infections. Preferably, the display of the specific individual/room on the alert display is made at the moment such determination is made. |
| System Database | A computer database that electronically stores records of all alerts generated, notifications, confirmation requests, responses, reconfirmation requests and any other desired information concerning the individual's entry, visit, movements, actions and/or exit within the patient's room. |
| Caregiver | A relative, friend, individual, company or facility whose purpose is to provide assistance in the care of daily living activities for individuals who are disabled, injured, elderly or otherwise in need of assistance. |

4. DETAILED DESCRIPTION OF DRAWINGS

Figure 1:
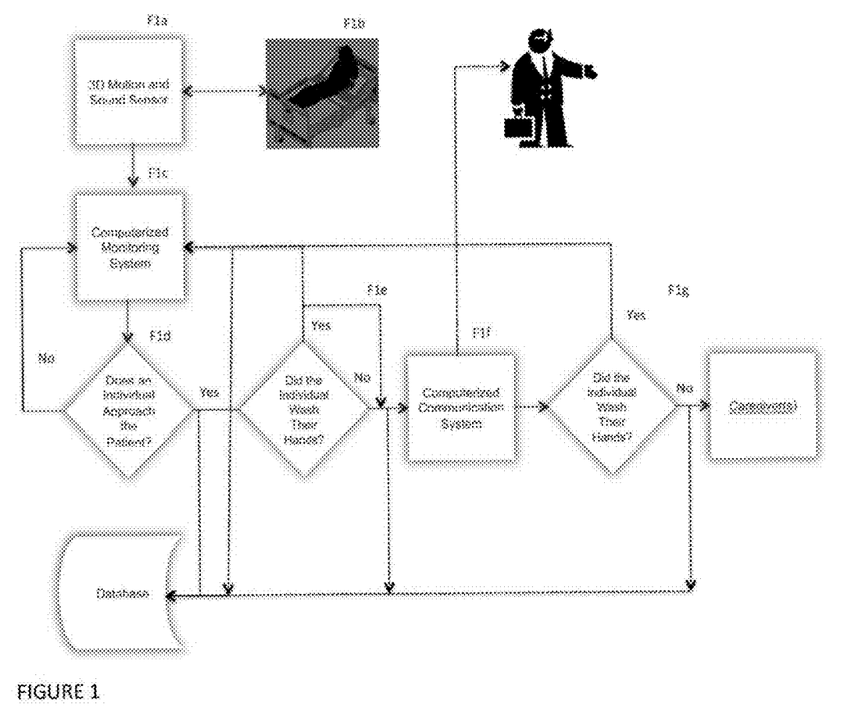
FIG. 1 is a workflow flowchart for monitoring and determining whether an individual who enters a patient's room takes the appropriate steps required (such as, but not limited to, washing his or her hands) prior to approaching the patient.

A hand-washing compliance determination for an individual entering a patient's room, prior to the individual approaching the patient is illustrated in FIG. 1. Hand-washing compliance is considered non-limiting and the system and method can be used to determine if the individual is compliant with other activities, appropriate measures or events prior, during or after approaching the patient, including, but not limited to, other activities that if not undertaken are also known to assist or aid in the spread of HAIs.

Specifically, FIG. 1 shows the workflow for monitoring whether an individual takes appropriate measures to prevent or reduce the spread of HAIs through the use of 3D Motion and Sound sensors. At step F1*a*, one or more 3D Motion and Sound sensors can be installed in a patient's room, home, hospital room, or other place of temporary or permanent residence. At step 1*b*, the one or more 3D Motion and Sound sensors can be configured to recognize the patient and other individuals using biometric identifiers such as facial recognition, height, distance between points on the body, etc. Alternatively or additionally, a virtual three-dimensional zone around the patient can be created through a software application portion of the system to define an area around the patient. When the individual is a certain predetermined distance from the area or enters the area can be recognized as the event for determining that the individual is approaching the patient. Once the patient is identified, the software application can also be programmed to automatically generate a configurable three-dimensional zone or perimeter around the patient that acts as a virtual barrier or event triggering boundary.

Furthermore, as the system can be programmed to recognize the patient as described above and below, the system can also be programmed to allow the virtual zone around the patient to follow the patient, if the patient moves around the room or out of the bed. As a non-limiting example, if the patient is sitting in a chair within the room, as the system recognizes the patient by the biometric identifiers, the location virtual zone can be shifted so that it remains around the patient while the patient sits in the chair. Accordingly, the determination of whether the individual is approaching the patient can be then made based on the patient's current position in the chair. Other non-limiting examples include the patient being in the restroom, the patient looking out their window, etc.

At step F1*c*, data (video and/or 3D depth data) from the one or more 3D Motion and Sound sensors are sent to a computerized monitoring system. At step F1*d*, when (or if) the computerized monitoring system detects or determines an individual, who is not the patient, entering or approaching the area (such as the virtual area discussed above) where a patient resides to approach the patient it will make a record in the database of such event and attempt to determine whether an appropriate measure has been taken by said individual to mitigate the spread of infection using one or more methods including but not limited to washing their hands or utilizing hand sanitation soaps, gels or lotions. Where the location of the hand sanitizer, sink, etc. is outside of the patient's room, one or more additional 3D Motion and Sound sensors can be positioned and configured in order to determine (capture) whether the individual washed and/or sanitized their hands prior to entering the patient's room. This captured video and/or 3D depth data can also be stored and/or reviewed by the Computerized Monitoring System when the system makes its determination. Depending on the setup of the particular room, the location of a 3D Motion and Sound sensor and/or the coverage area seen capabilities of the 3D Motion and Sound sensor, it is possible that a single 3D Motion and Sound sensor may be able to provide information concerning the patient's defined virtual zone and also provide the information regarding whether the individual washed his or her hands, etc. Adding one or more additional 3D Motion and Sound sensors outside of the patient's room also allows the system to recognize that a non-patient individual is entering the patient's room sooner to permit more time for the system to monitor the non-patient individual.

"Washing hands", "Washing his or her hands", etc. shall be defined to include traditional hand washing, hand sanitizing, etc.

A record can also be electronically entered in a database to record a lack of compliance and/or compliance by the individual. Where the individual is in compliance, the computerized monitoring system will continually monitor the data (video and/or 3D depth data) being sent from the one or more 3D motion and sound sensors. Additionally, where a lack of compliance is detected, the computerized monitoring system can be programmed to automatically begin, or manually restarted to begin, again monitoring data from the one or more 3D motion and sound sensors. However, at all times during operating the 3D motion and sound sensors are on and are capturing, recording and/or streaming video and/or 3D depth data from the room and/or just outside the room, and do not require a triggering event to initiate recording.

At step F1*e*, when the system detects that an appropriate action has been taken by the individual to mitigate the spread of infections, a record can be made in the database and audible and/or visible alerts can be issued to the individual acknowledging said compliance. At step F1*f*, should the individual continue to approach or remain in the vicinity of the patient without having taken appropriate steps to mitigate the spread of infections, an audible and/or visible alert to such individual, notifying said individual of the need to take preventative measures to prevent or reduce the spread of infections can be sent by the computerized communication system. Other personal notifications to the individual can also be sent such as calling the individuals cell phone or smart phone, sending a text message, calling the individual's pager, etc. The system can monitor, using gesture recognition, location tracking or other measures whether said individual has taken appropriate steps to mitigate the spread of infection such as washing their hands or utilizing hand sanitation soaps, gels or lotions. Particularly with location tracking, virtual zones can also be defined around the hand washing sink, to determine or detect if the individual entered the sink zone prior to approaching the patient. It is also within the scope of the invention, to provide a water flow sensor which can be in electronic communication (wired or wireless) with one or more components of the system (i.e. computerized monitoring system). The water flow sensor can be provided or in communication with the water flow line of the sink, such that when the hot and/or cold water valve of the sink is opened to permit water flow into the sink, the sensor sends a signal representing such information to the system.

The system determines whether one of the hand sanitization events has occurred by creating a configurable three-dimensional zone or perimeter around the sink or other such equipment in the patient's room utilized for hand sanitization. The individual entering the room and approaching the patient's virtual barrier must first be observed entering the hand sanitization zone and performing a hand-sanitization event such as specific gestures indicative of hand sanitization (i.e. rubbing hands together in a washing motion or pressing a lever to dispense sanitizing gel or lotions), visual confirmation of soap, gel, or lotion dispensing by the dispensing device or proximity location to such hand sanitization devices. The 3D Motion and Sound sensor locks on the individual and can send back to the computerized monitoring system the 3D coordinates of the joints in the individual's body and a skeletal outline of the person. The system is also able to recognize gestures such as waving a hand, rubbing hands together, etc. and uses the information received from the 3D Motion and Sound Sensor to determine if the individual is in the hand wash zone, bed zone, etc., how long the joint has been in that zone and what if any gestures the individual is doing.

At step F1g, if the individual approaching the patient or within close proximity to the patient fails to comply with the audible and/or visible warnings to comply, notification can be given to the caregivers, individual's employer and/or other designated persons that the individual has failed to comply. Notification of caregivers can be made through phone call, text messaging, speakerphone systems, email, or other electronic means of communication. The system database can also be updated to reflect actions taken.

Where an individual breathing on the patient is also an issue for the particular patient and/or whether exposure to a patient with an infectious disease is an issue, the Computerized Monitoring System can also be programmed to determine whether or not the individual is wearing a mask. The present invention method would go through similar steps of monitoring and notification as described above for the "hand washing" monitoring. Though "mask" monitoring preferably would be in addition to "hand washing" monitoring, it is within the scope of the invention that the system is also programmed to monitor "mask" monitoring, without "hand washing" monitoring. Similarly, if the individual is required to be wearing gloves, similar steps can also be performed to confirm compliance or alert for non-compliance.

Figure 2:
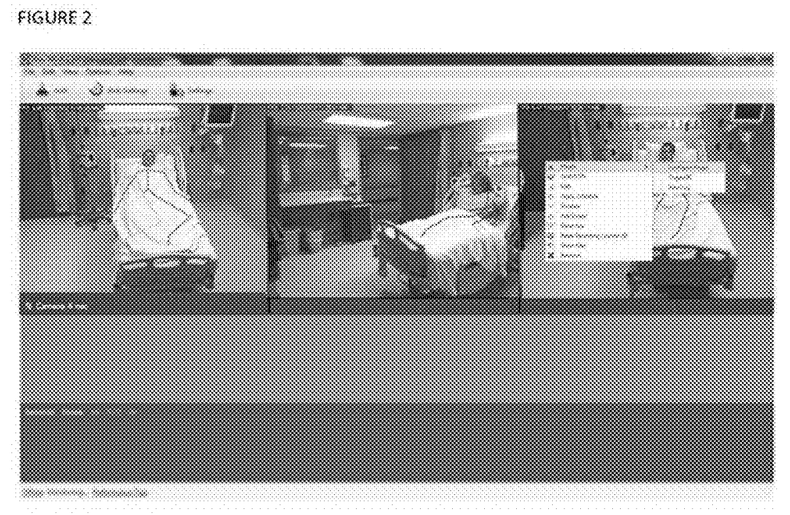
FIGS. 2 through 14 illustrate various screen shots for configuring the system for operation.
Figure 3:
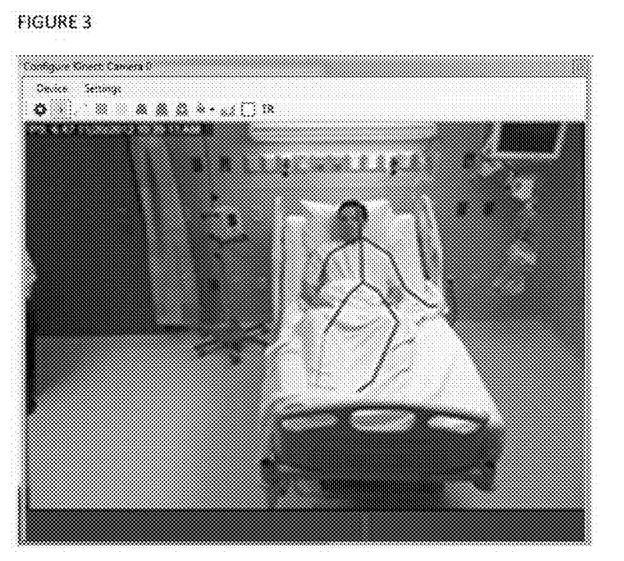

FIGS. 2 through 14 illustrate several set up screen shots for configuring the virtual zones and alert types. In FIG. 2, the bed zone can be configured for a given or specific 3D Motion and Sound Sensor. To begin configuration, the user can hover over the 3D Motion and Sound Sensor video window with the cursor, right-click, select plugin and then select configure plug-in. A window will popup showing the 3D Motion and Sound Sensors' feed. The user selects the icon for the type of zone they wish to draw, which as a non-limiting example and illustrative purposes, can be a bed zone (See FIG. 3). Similar steps are taken for creating the above-mentioned virtual sink zone, where provided.

Figure 4:
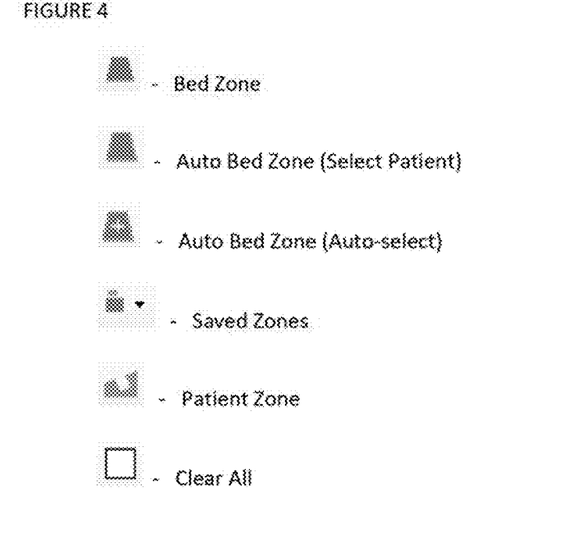

As non-limiting examples, the icons that appear on the screen for selection can include the following symbols shown in FIG. 4. In this non-limiting example, in no particular order, some of the icons include, Bed Zone, Auto Bed Zone (Select Patient), Auto Bed Zone (Auto-select), Saved Zones, and Clear All.

Figure 5:
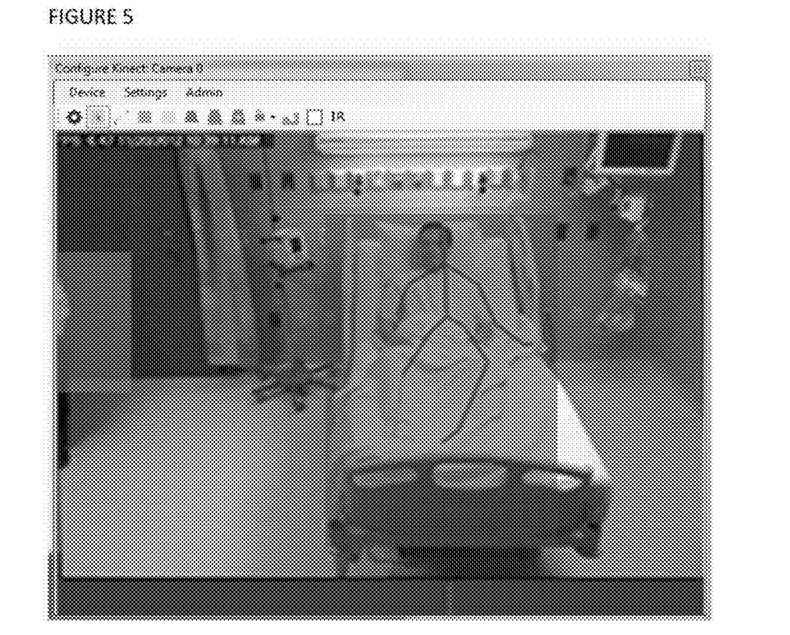
Figure 7:
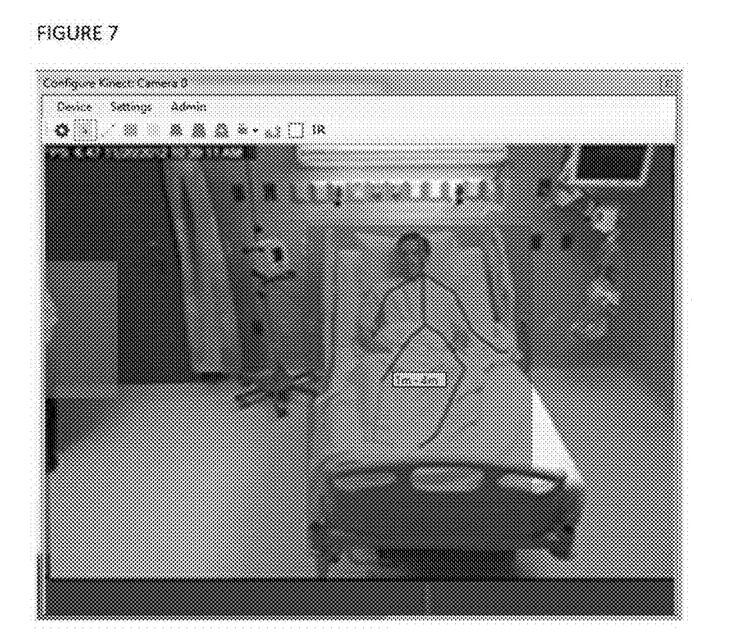

As seen in FIG. 5, to place a zone, the user clicks on the screen where he or she would like to start the zone. Then, the cursor is moved to the corner point for zone and clicked again. The user continues to select additional points until the zone is drawn to the user's satisfaction. Preferably, the user clicks on the round end point of the beginning of the zone to complete the zone (See FIG. 5). When the zone has been completed, the zone can appear and a depth range box (i.e. square, rectangle, etc. disposed over the patient on the screen) can be provided on the screen, such as, but not limited to, in the middle of the screen or zone (see FIG. 7), though any location on the screen is considered within the scope of the invention. As seen in FIG. 7, upon completion the zone appears and has a depth range box preferably in the middle.

Figure 6:
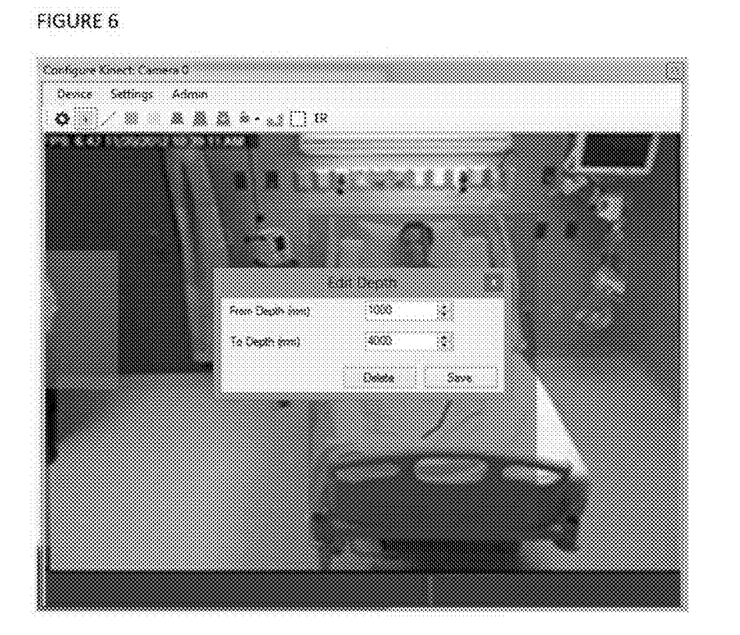

As seen in FIG. 6, the user can adjust the depth range for any given zone. By preferably double clicking on the depth range box or by other conventional selection methods an Edit Depth window can appear. The user can enter in the depth ranges (preferably in millimeters (mm) though not considered limiting) and then the user can click the Save button or icon when done to store the entered values.

If there are any other types of zones to draw for the particular sensor, the above steps are repeated to place the next zone and the depth setting can be adjusted for each if necessary. Additionally, all zones can be cleared by clicking on or otherwise selecting the Clear All icon in the toolbar. Once all of the zones/wires are configured, the user can close the window to finish or can be provided with the option to save the zone configuration for later use.

Figure 8:
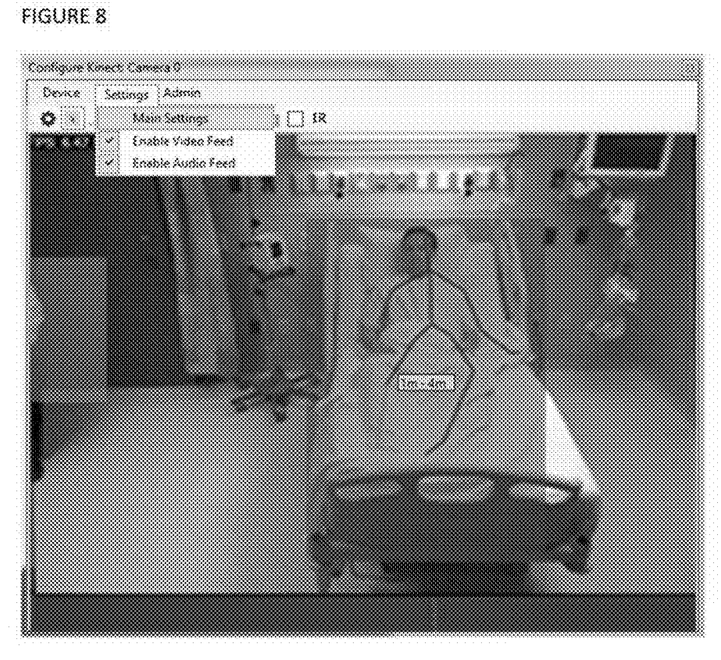

As seen in FIG. 8, to access the main settings window, the user can click or otherwise select the Settings menu and the select Main Settings from the drop-down list. As one non-limiting alternative, the user can click on the Gear icon ( ) or other designated icon in the toolbar to access the main settings window.

Figure 9:
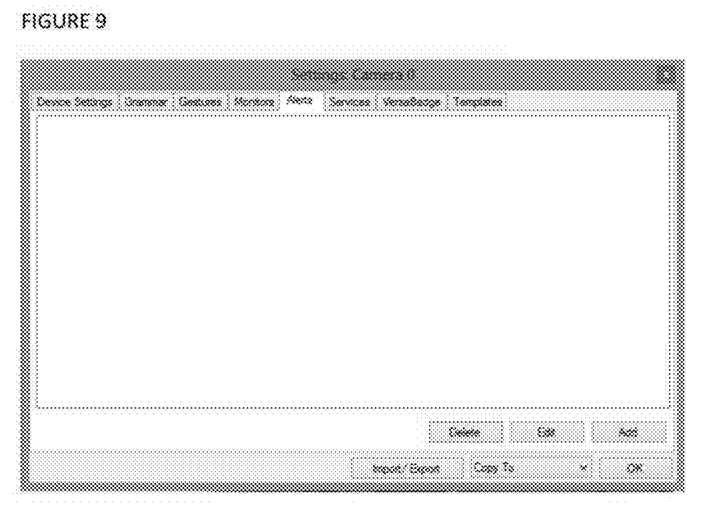
Figure 10:
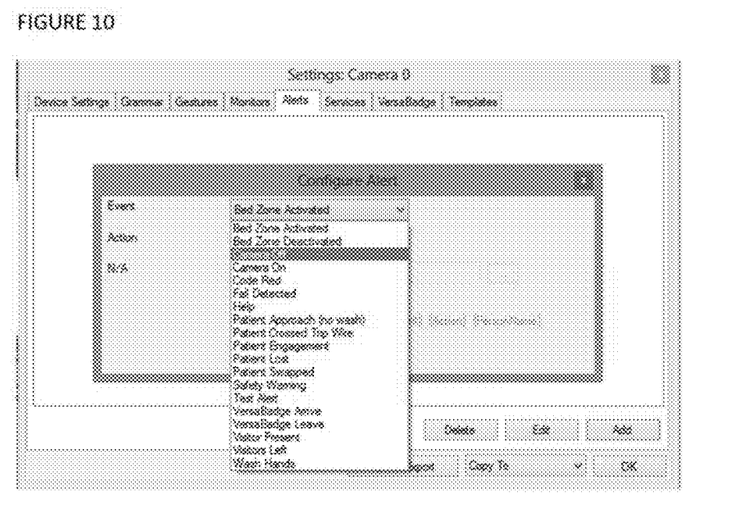

As seen in FIG. 9, for one non-limiting way to configure a new Alert, the user can select the Alerts tabs and then click on or otherwise select the Add button, which can result in the Configure Alert box appearing on the screen (See FIG. 10). As seen in FIG. 10, under the Event field, the user can then select the event from the drop down list that the user wishes to send an alert on. Though not shown, the dropdown list can include an alert for non-compliance with hand washing, non-compliance for not wearing breathing mask, etc.

Figure 11:
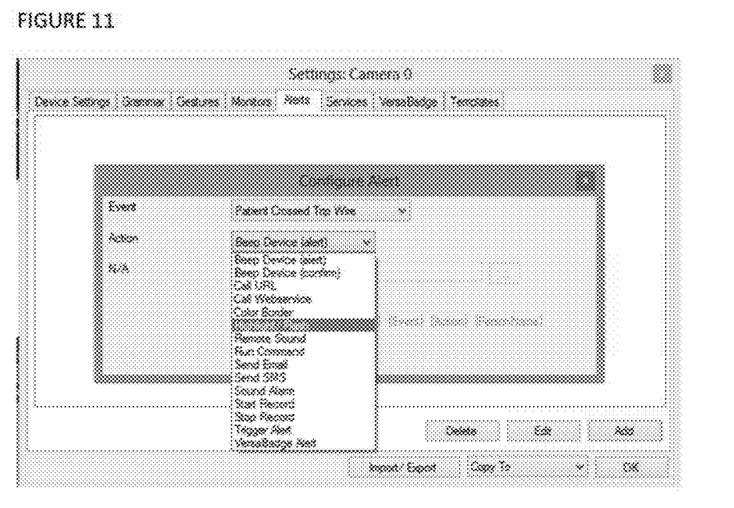
Figure 12:
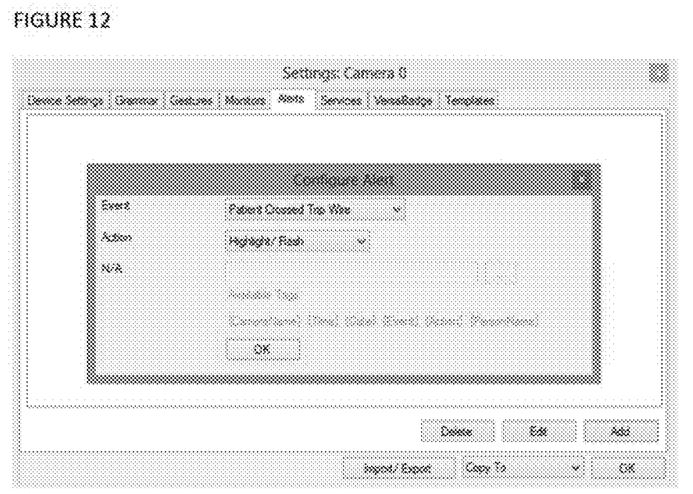
Figure 13:
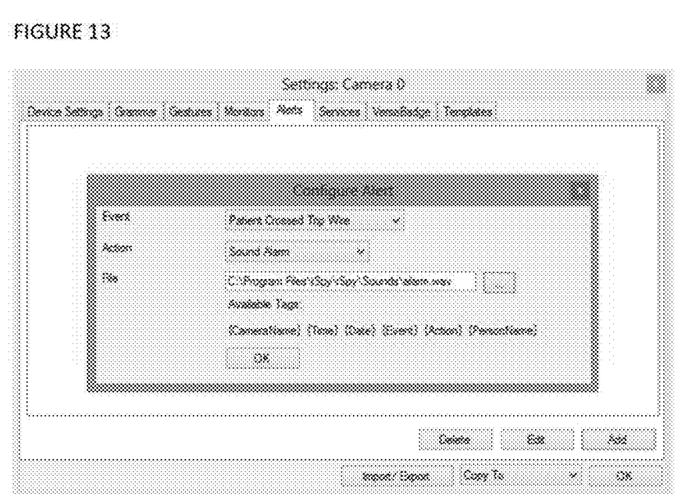
Figure 14:
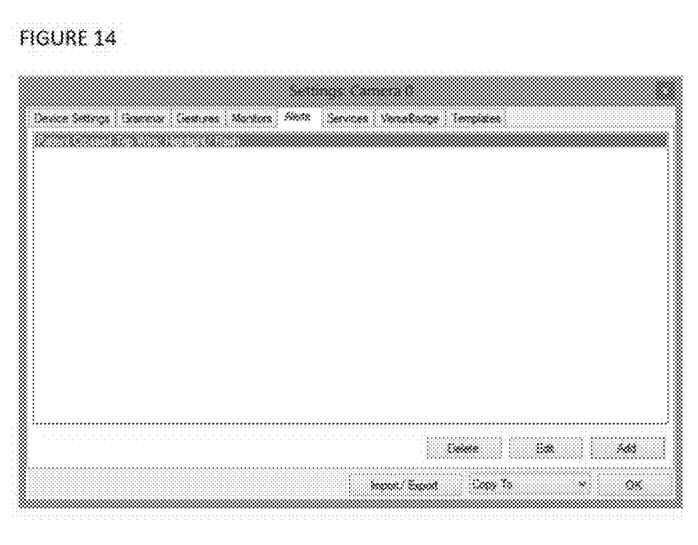

As seen in FIG. 11, once the Event type is selected, under the Action field, the user can select the Action he or she wishes to have the system perform when the selected Event is detected or determined. Once the Event and Action have been selected the OK button (See FIG. 12) can be selected to save the selected entries.

For certain Actions an additional field may need to be completed to finish the Action. If the field is required, it can appear below the Action dropdown (See FIG. 13). If no further fields are required, the Configure Alert box can display N/A (See FIG. 12) or just be blank. As mentioned above, once all settings are selected, the user clicks or otherwise selects the OK button, which causes the new Alert to be listed in the Alerts tab window. To edit an existing Alert, the user first clicks on or otherwise selects the Alert and then selects the Edit button (See FIG. 14). To delete an Alert, first highlight it and then click on the Delete button (See FIG. 14).

To add more Alerts, the user clicks or selects the Add button and repeats the above described steps. Once finished, the user clicks on or otherwise selects the bottom corner OK button to save and close the window.

Figure 15:
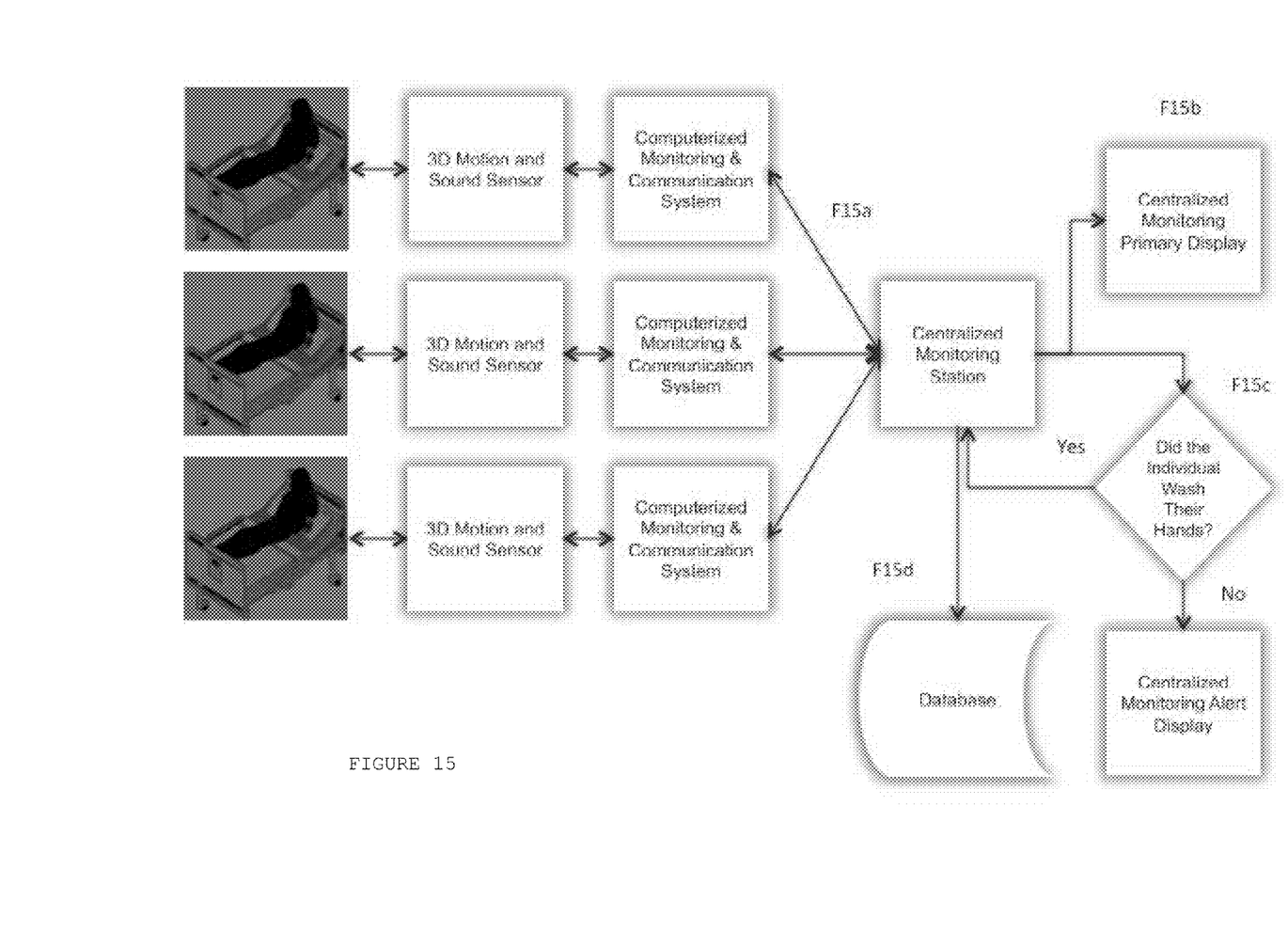
FIG. 15 is a block diagram and workflow of the centralized monitoring and alerting system in accordance with the disclosure.

FIG. 15 illustrates a block diagram for centralized monitoring and alerting and shows the workflow for centralized monitoring and alerting regarding whether an individual takes appropriate measures to prevent or reduce the spread of HAIs based on information sent from the use of 3D Motion and Sound sensors. One or more 3D Motion and Sound sensors are installed in and/or just outside an individual's room, home, hospital room, or other place of temporary or permanent residence and connected to the computerized monitoring and communication systems as described in FIG. 1. At step F15a the video, audio, 3D depth and/or alert data from the sensor(s) can be sent to a centralized monitoring station by the computerized monitoring and communication systems where the data is aggregated. Preferably, the centralized monitoring station receives data at all times transmitted, sent or broadcasted from the sensors to allow the room and/or various individuals to be constantly monitored at the centralized station while they are in the patient's room, regardless of whether or not an individual takes appropriate measures to prevent or reduce the spread of HAIs.

At step F15b, all video, audio, 3D depth and/or alert feeds received by the centralized monitoring station can be displayed on the centralized monitoring primary display. Alternatively, multiple centralized monitoring primary displays can be utilized based on the quantity of rooms to be monitored at a given time. At step F15c, when the centralized monitoring system receives an alert from any of the computerized monitoring and communication systems indicating that an individual in any of the monitored rooms or other locations has not taken appropriate measures to prevent or reduce the spread of HAIs, the video, audio, 3D depth data and/or alert information can be displayed on the Centralized Monitoring Alert Display for the specific patient's room. Should the centralized monitoring station receive alerts from more then one of the computerized monitoring and communication systems indicating that an individual in a monitored room or location has not taken appropriate measures to prevent the spread of HAIs, the centralized monitoring alert display will display the video, audio, 3D depth data and/or alerting information from all such instances at the same time. If no alert is received by the centralized monitoring station, preferably nothing is displayed on the Centralized Monitoring Alert Display. At step F15d, an electronic record of any alerts received by the Centralized Monitoring Station can be stored in an electronic database, which is in communication with the Centralized Monitoring Station.

It is also within the scope of the disclosure, that only a Centralized Monitoring Alert Display is provided which is in direct communication with the computerized monitoring and communication system. In this embodiment, when a sanitary violation (as described above) occurs the information, 3D depth data and/or video is directly sent to the Centralized Monitoring Alert Display by the Computerized monitoring system.

The above described system uses several components, including, but not limited to:

1. One or more 3D Motion and Sound Sensors. However, it also within the scope of the invention to eliminate the sound sensor and have the functions of the invention be performed with only 3D motion sensors that are continuously on and record, capture and/or stream video and/or 3D depth data;
2. Computerized Monitoring System in electronic communication with the one or more 3D Motion and Sound Sensors;
3. Computerized Communication System in electronic communication with the Computerized Monitoring System;
4. Centralized Monitoring Station in electronic communication with one or more 3D Motion and Sound sensors, Computerized Monitoring and Computerized Communication Systems;
5. Centralized Monitoring Primary Display in electronic communication with one or more Centralized Monitoring Stations;
6. Centralized Monitoring Alert Display in electronic communication with one or more Centralized Monitoring Stations; and/or
7. Database The various components can be in electrical, wired and wireless communication with each other. Located remote is defined to mean that the centralized monitoring station, centralized monitoring primary display and/or centralized monitoring alert display is not physically located within the monitored rooms. However, the location can be on the same premises at a different location (i.e. nurse station for the premises, hospital, etc.) or a different location (i.e. monitoring station, etc.).

The automatic detection and notification or individuals who do not take appropriate steps to prevent or reduce the spread of infections will provide significant administrative and clinical benefits to caregivers and individuals alike, including, but not limited to, the following public benefits:

1. Automation of preventative measure detection and notification of caregivers or other designated entities.
2. Reduction in incidences of HAIs.
3. Increased survival rate for individuals who are susceptible to HAIs
4. Reduction in costs for hospitalization and medical care related to HAIs.

All components of the present invention system and their locations, electronic communication methods between the system components, electronic storage mechanisms, etc. discussed above or shown in the drawings, if any, are merely by way of example and are not considered limiting and other component(s) and their locations, electronic communication methods, electronic storage mechanisms, etc. can be chosen and used and all are considered within the scope of the invention.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the invention has been described and disclosed in certain terms and has disclosed certain embodiments or modifications, persons skilled in the art who have acquainted themselves with the invention, will appreciate that it is not necessarily limited by such terms, nor to the specific embodiments and modification disclosed herein. Thus, a wide variety of alternatives, suggested by the teachings herein, can be practiced without departing from the spirit of the invention, and rights to such alternatives are particularly reserved and considered within the scope of the invention.

What is claimed is:

1. A method for detecting whether an individual who enters a room of a patient washes his or her hands prior to approaching the patient, said method comprising the steps of:
   (a) configuring a virtual patient zone defining an area around a patient who is located within a room;
   (b) providing one or more 3D motion and sound sensors to capture live video data from the area;
   (c) forwarding the video data from the one or more 3D motion and sound sensors to a computerized monitoring system;
   (d) determining by the computerized monitoring system from the received video data when an individual is a certain distance from the area or has entered the area;

(e) determining by the computerized monitoring system from the received video data whether the individual washed his or her hands where it is determined in step (d) that the individual is within a certain distance from the area or within the area;

(f) electronically transmitting an alert or notification to the individual by a computerized communication system when the computerized monitoring system determines that the individual did not wash his or her hands in step (e); and (g) electronically transmitting an alert or notification to a centralized monitoring system by the computerized monitoring system when the computerized monitoring system determines that the individual did not wash his or her hands in step (e).

2. The method for detecting of claim 1 further comprising the step of updating a database in communication with the computerized monitoring system regarding the determination that the individual did not wash his or her hands prior to being within a certain distance from the area or within the area.

3. The method for detecting of claim 1 further comprising the step of notifying a previously designated caregiver by electronic message regarding the determination that the individual did not wash his or her hands prior to being within a certain distance from the area or within the area.

4. The method for detecting of claim 1 wherein step (a) comprises the steps of
(i) selecting a patient zone from a choice of icons appearing on a screen of a display where the live video feed from the one or more 3D motion and sound sensors is visible on the screen;
(ii) using an electronic cursor clicking on the screen where the patient zone begins to create an end point;
(iii) moving the electronic cursor to a corner point for the patient zone and clicking on the screen with the electronic cursor; and
(iv) repeating step (iii) for the remaining corner points for the patient zone and clicking on the end point with the electronic cursor to complete the virtual patient zone.

5. The method for detecting of claim 4 further comprising the step of displaying a depth range box.

6. The method for detecting of claim 5 wherein the depth range box is displayed on the screen within a portion of the completed virtual patient zone.

7. The method for detecting of claim 1 further comprising the step of continuously displaying a live video feed of the monitored area received from the one or more 3D motion and sound sensors on a centralized monitoring primary display that is remotely located from the monitored area.

8. The method for detecting of claim 1 further comprising the step of continuously displaying a live video feed of the monitored area for a specific room received from the one or more 3D motion and sound sensors on a centralized monitoring alert display after it has been determined that the individual in the specific room did not wash his or her hands in step (e).

9. The method for detecting of claim 1 wherein the one or more 3D motion and sound sensors are programmed to lock on the patient and forward data to the computerized monitoring system representing 3D coordinates of body joints for the patient and a general skeletal outline of the monitored individual such that as the patient moves within a viewing range of the one or more 3D motion and sound sensors the configured virtual patient zone is virtually moved by the computerized monitoring system so that the virtual patient zone remains around the patient based on the patient's current location within the room.

10. The method for detecting of claim 9 wherein the computerized monitoring system determines if the individual is within a certain distance of the patient zone or within the patient zone by the location of specific body segments of the individual being within a certain predetermined or preconfigured distance from the patient zone or located in the virtual patient zone.

11. A method for detecting when an individual who enters a room of a patient washes his or her hands prior to approaching the patient, said method comprising the steps of:

(a) configuring a virtual patient zone defining an area around a patient who is located within a room;
(b) providing one or more 3D motion and sound sensors to capture live video and 3D depth data from the area;
(c) electronically forwarding the video and 3D depth data from the one or more 3D motion and sound sensors to a computerized monitoring system located within the room;
(d) determining by the computerized monitoring system from the received video and 3D depth data when an individual is a certain distance from the area or has entered the defined area by location of specific body segments of the individual being within a certain predetermined or preconfigured distance from the patient zone or located in the virtual patient zone;
(e) determining by the computerized monitoring system from the received video and 3D depth data whether the individual washed his or her hands where it is determined in step (d) that the individual is within a certain distance from the area or within the area;
(f) electronically transmitting an alert or notification to the individual by a computerized communication system when the computerized monitoring system determines that the individual did not wash his or her hands in step (e); and
(g) electronically transmitting an alert or notification to a centralized monitoring system by the computerized monitoring system when the computerized monitoring system determines that the individual did not wash his or her hands in step (e).

12. The method for detecting of claim 11 further comprising the step of continuously displaying a live video feed of the monitored area received from the one or more 3D motion and sound sensors on a centralized monitoring primary display that is remotely located from the monitored area.

13. The method for detecting of claim 11 further comprising the step of continuously displaying a live video feed of the monitored area for a specific room received from the one or more 3D motion and sound sensors on a centralized monitoring alert display after it has been determined that the individual in the specific room did not wash his or her hands in step (e).

14. The method for detecting of claim 11 further comprising the step of notifying a previously designated caregiver by electronic message regarding the determination that the individual did not wash his or her hands prior to being within a certain distance from the area or within the area.

15. The method for detecting of claim 11 wherein step (a) comprises the steps of:
(i) selecting a patient zone from a choice of icons appearing on a screen of a display where the live video feed from the one or more 3D motion and sound sensors is visible on the screen;

(ii) using an electronic cursor clicking on the screen where the patient zone begins to create an end point;
(iii) moving the electronic cursor to a corner point for the patient zone and clicking on the screen with the electronic cursor; and
(iv) repeating step (iii) for the remaining corner points for the patient zone and clicking on the end point with the electronic cursor to complete the virtual patient zone.

16. The method for detecting of claim 15 further comprising the step of displaying a depth range box on the screen within a portion of the completed virtual patient zone.

17. The method for detecting of claim 11 wherein the one or more 3D motion and sound sensors are programmed to lock on the patient and forward data to the computerized monitoring system representing 3D coordinates of body joints for the patient and a general skeletal outline of the monitored individual such that as the patient moves within a viewing range of the one or more 3D motion and sound sensors the configured virtual patient zone is virtually moved by the computerized monitoring system so that the virtual patient zone remains around the patient based on the patient's current location within the room.

18. A method for detecting when an individual who enters a room of a patient washes his or her hands prior to approaching the patient, said method comprising the steps of:
(a) configuring a virtual patient zone defining an area around a patient who is located within a room;
(b) providing one or more 3D motion and sound sensors to capture live video and 3D depth data from the area;
(c) electronically forwarding the video and 3D depth data from the one or more 3D motion and sound sensors to a computerized monitoring system located within the room;
(d) determining by the computerized monitoring system from the received video and 3D depth data when an individual is a certain distance from the area or has entered the defined area by location of specific body segments of the individual being within a certain predetermined or preconfigured distance from the patient zone or located in the virtual patient zone;
(e) determining by the computerized monitoring system from the received video and 3D depth data whether the individual washed his or her hands where it is determined in step (d) that the individual is within a certain distance from the area or within the area;
(f) electronically transmitting an alert or notification to the individual by a computerized communication system when the computerized monitoring system determines that the individual did not wash his or her hands in step (e);
(g) electronically transmitting an alert or notification to a centralized monitoring system by the computerized monitoring system when the computerized monitoring system determines that the individual did not wash his or her hands in step (e);
(h) continuously displaying a live video feed of the monitored area received from the one or more 3D motion and sound sensors for a plurality of separate rooms being monitored on a centralized monitoring primary display that is remotely located from the monitored area; and
(i) continuously displaying a live video feed of the monitored area for a specific room received from the one or more 3D motion and sound sensors on a centralized monitoring alert display after it has been determined that the individual in the specific room did not wash his or her hands in step (e).

19. The method for detecting of claim 18 further comprising the step of virtually moving the configured virtual patient zone by the computerized monitoring system when it is determined by the computerized monitoring system that the patient has moved within the room so that the virtual patient zone remains around the patient based on the patient's current location within the room.

20. The method for detecting of claim 18 wherein step (a) comprises the steps of:
(i) selecting a patient zone from a choice of icons appearing on a screen of a display where the live video feed from the one or more 3D motion and sound sensors is visible on the screen;
(ii) using an electronic cursor clicking on the screen where the patient zone begins to create an end point;
(iii) moving the electronic cursor to a corner point for the patient zone and clicking on the screen with the electronic cursor;
(iv) repeating step (iii) for the remaining corner points for the patient zone and clicking on the end point with the electronic cursor to complete the virtual patient zone.

* * * * *

UNITED STATES PATENT AND TRADEMARK OFFICE
CERTIFICATE OF CORRECTION

PATENT NO.         : 9,729,833 B1                                    Page 1 of 1
APPLICATION NO.    : 14/613866
DATED              : August 8, 2017
INVENTOR(S)        : Neil Kusens It is certified that error appears in the above-identified patent and that said Letters Patent is hereby corrected as shown below:

In the Claims

Column 11, Line 28: Please remove "of" and replace with --of:--.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*